United States Patent
Buller et al.

(10) Patent No.: US 12,337,125 B2
(45) Date of Patent: Jun. 24, 2025

(54) GUIDEWIRE FIXATION

(71) Applicant: Teleflex Life Sciences LLC, Wilmington, DE (US)

(72) Inventors: Christopher E. Buller, Toronto (CA); Chad Kugler, Buffalo, MN (US); Dean Peterson, Minneapolis, MN (US); Joshua Brenizer, Oak Grove, MN (US); Danny M. Jester, Eden Prairie, MN (US)

(73) Assignee: Teleflex Life Sciences LLC, Wilmington, DE (US)

( * ) Notice: Subject to any disclaimer, the term of this patent is extended or adjusted under 35 U.S.C. 154(b) by 1048 days.

(21) Appl. No.: 17/201,810

(22) Filed: Mar. 15, 2021

(65) Prior Publication Data
US 2021/0196928 A1 Jul. 1, 2021

Related U.S. Application Data

(63) Continuation of application No. 15/163,044, filed on May 24, 2016, now Pat. No. 10,974,028.
(Continued)

(51) Int. Cl.
*A61M 25/01* (2006.01)
*A61M 25/02* (2006.01)
(Continued)

(52) U.S. Cl.
CPC ........ *A61M 25/0169* (2013.01); *A61M 25/01* (2013.01); *A61M 25/09041* (2013.01);
(Continued)

(58) Field of Classification Search
CPC ...... A61M 25/0662; A61M 2025/0681; A61M 2025/09125; A61M 25/0169
See application file for complete search history.

(56) References Cited

U.S. PATENT DOCUMENTS

| 4,000,739 A | 1/1977 | Stevens |
| 4,166,468 A | 9/1979 | Haynie |

(Continued)

FOREIGN PATENT DOCUMENTS

| CA | 2008784 C | 7/2002 |
| DE | 69928825 | 7/2006 |

(Continued)

OTHER PUBLICATIONS

Bertrand, Michel E. "The Evolution Of Cardiac Catheterization and Interventional Cardiology," European Society of Cardiology, 2006, 10 pages.

(Continued)

*Primary Examiner* — Scott J Medway
(74) *Attorney, Agent, or Firm* — Dorsey & Whitney LLP

(57) ABSTRACT

Percutaneous devices and methods for releasably engaging a guidewire against an inner surface of a tubular member are disclosed. A percutaneous device can include a tube member, a push member, and a fixation mechanism such as a fixation balloon. The tube member can define a lumen sized and shaped to receive one or more interventional medical devices therethrough and can have an outer diameter smaller than a lumen of a guide catheter. The push member can extend proximal of the tube member for slidably positioning a distal end portion of the tube member within and beyond a distal end of the guide catheter. The push member can include a lumen in fluid communication with an interior of the fixation balloon, for example, for delivering inflation fluid to, or removing fluid from, the balloon. The fixation balloon can be positioned can be positioned and configured to engage a guidewire against the inner surface of the guide catheter or of the tube member when inflated.

19 Claims, 7 Drawing Sheets

Related U.S. Application Data

(60) Provisional application No. 62/190,879, filed on Jul. 10, 2015, provisional application No. 62/166,259, filed on May 26, 2015.

(51) Int. Cl.
*A61M 25/06* (2006.01)
*A61M 25/09* (2006.01)

(52) U.S. Cl.
CPC . *A61M 25/0108* (2013.01); *A61M 2025/0293* (2013.01); *A61M 25/0662* (2013.01); *A61M 2025/09125* (2013.01)

(56) References Cited

U.S. PATENT DOCUMENTS

| | | |
|---|---|---|
| 4,289,128 A | 9/1981 | Rusch |
| 4,723,936 A | 2/1988 | Buchbinder et al. |
| 4,762,129 A | 8/1988 | Bonzel |
| 4,813,930 A | 3/1989 | Elliott |
| 4,832,028 A | 5/1989 | Patel |
| 4,838,268 A | 6/1989 | Keith et al. |
| 4,838,269 A | 6/1989 | Robinson et al. |
| 4,909,252 A | 3/1990 | Goldberger |
| 4,921,483 A | 5/1990 | Wijay et al. |
| 4,932,413 A | 6/1990 | Shockey et al. |
| 4,943,278 A | 7/1990 | Euteneuer et al. |
| 4,946,440 A | 8/1990 | Hall |
| 4,994,745 A | 2/1991 | Mizuta |
| 5,002,531 A | 3/1991 | Bonzel |
| 5,040,548 A | 8/1991 | Yock |
| 5,061,273 A | 10/1991 | Yock |
| 5,074,845 A | 12/1991 | Miraki et al. |
| 5,098,412 A | 3/1992 | Shiu |
| 5,102,403 A | 4/1992 | Alt |
| 5,120,323 A | 6/1992 | Shockey et al. |
| 5,122,125 A | 6/1992 | Deuss |
| 5,156,594 A | 10/1992 | Keith |
| 5,232,445 A | 8/1993 | Bonzel |
| 5,234,416 A | 8/1993 | Macaulay et al. |
| 5,257,974 A | 11/1993 | Cox |
| 5,267,958 A | 12/1993 | Buchbinder et al. |
| 5,290,247 A | 3/1994 | Crittenden |
| 5,328,472 A | 7/1994 | Steinke et al. |
| 5,344,401 A | 9/1994 | Radisch et al. |
| 5,350,395 A | 9/1994 | Yock |
| 5,368,567 A | 11/1994 | Lee |
| 5,383,853 A | 1/1995 | Jung et al. |
| 5,395,389 A | 3/1995 | Patel |
| 5,413,560 A | 5/1995 | Solar |
| 5,415,639 A | 5/1995 | VandenEinde et al. |
| 5,439,445 A | 8/1995 | Kontos |
| 5,441,489 A | 8/1995 | Utsumi et al. |
| 5,445,624 A | 8/1995 | Jimenez |
| 5,445,625 A | 8/1995 | Voda |
| 5,451,209 A | 9/1995 | Ainsworth et al. |
| 5,472,425 A | 12/1995 | Teirstein |
| 5,484,409 A | 1/1996 | Atkinson et al. |
| 5,489,278 A | 2/1996 | Abrahamson |
| 5,527,292 A | 6/1996 | Adams et al. |
| 5,531,721 A | 7/1996 | Pepin et al. |
| 5,545,149 A | 8/1996 | Brin et al. |
| 5,549,553 A | 8/1996 | Ressemann et al. |
| 5,562,620 A | 10/1996 | Klein et al. |
| 5,567,203 A | 10/1996 | Euteneuer et al. |
| 5,571,087 A | 11/1996 | Ressemann et al. |
| 5,578,009 A | 11/1996 | Kraus et al. |
| 5,599,326 A | 2/1997 | Carter |
| 5,620,417 A | 4/1997 | Jang et al. |
| 5,649,909 A | 7/1997 | Cornelius |
| 5,658,263 A | 8/1997 | Dang et al. |
| 5,658,309 A | 8/1997 | Berthiaume et al. |
| 5,690,613 A | 11/1997 | Verbeek |
| 5,704,926 A | 1/1998 | Sutton |
| 5,720,300 A | 2/1998 | Fagan et al. |
| 5,720,724 A | 2/1998 | Ressemann et al. |
| 5,743,876 A | 4/1998 | Swanson |
| 5,755,704 A | 5/1998 | Lunn |
| 5,772,642 A | 6/1998 | Ciamacco et al. |
| 5,776,141 A | 7/1998 | Klein et al. |
| 5,785,685 A | 7/1998 | Kugler et al. |
| 5,792,124 A | 8/1998 | Horrigan et al. |
| 5,843,022 A | 12/1998 | Willard et al. |
| 5,860,963 A | 1/1999 | Azam et al. |
| 5,891,056 A | 4/1999 | Ramzipoor |
| 5,902,290 A | 5/1999 | Peacock et al. |
| 5,911,715 A | 6/1999 | Berg et al. |
| 5,919,162 A * | 7/1999 | Burns ............... A61M 25/0075 604/99.01 |
| 5,961,510 A | 10/1999 | Fugoso et al. |
| 5,980,486 A | 11/1999 | Enger |
| 6,042,578 A | 3/2000 | Dinh et al. |
| 6,071,273 A | 6/2000 | Euteneuer et al. |
| 6,102,890 A | 8/2000 | Stivland et al. |
| 6,159,195 A | 12/2000 | Ha et al. |
| 6,190,358 B1 | 2/2001 | Fitzmaurice et al. |
| 6,193,686 B1 | 2/2001 | Estrada et al. |
| 6,199,262 B1 | 3/2001 | Martin |
| 6,245,053 B1 | 6/2001 | Benjamin |
| 6,270,465 B1 | 8/2001 | Keith et al. |
| 6,299,628 B1 | 10/2001 | Harrison et al. |
| 6,338,725 B1 | 1/2002 | Hermann et al. |
| 6,398,773 B1 | 6/2002 | Bagaoisan et al. |
| 6,409,863 B1 | 6/2002 | Williams et al. |
| 6,443,912 B1 | 9/2002 | Mazzola et al. |
| 6,475,195 B1 | 11/2002 | Voda |
| 6,488,655 B1 | 12/2002 | Wantink et al. |
| 6,503,223 B1 | 1/2003 | Sekido et al. |
| 6,503,353 B1 | 1/2003 | Peterson et al. |
| 6,548,010 B1 | 4/2003 | Stivland et al. |
| 6,575,958 B1 | 6/2003 | Happ et al. |
| 6,591,472 B1 | 7/2003 | Noone et al. |
| 6,595,952 B2 | 7/2003 | Forsberg |
| 6,610,068 B1 | 8/2003 | Yang |
| 6,620,149 B1 | 9/2003 | Lenz et al. |
| 6,626,889 B1 | 9/2003 | Simpson et al. |
| 6,635,029 B1 | 10/2003 | Venturelli |
| 6,638,268 B2 | 10/2003 | Niazi |
| 6,648,874 B2 | 11/2003 | Parisi et al. |
| 6,689,144 B2 | 2/2004 | Gerberding |
| 6,706,018 B2 | 3/2004 | Westlund et al. |
| 6,733,487 B2 | 5/2004 | Keith et al. |
| 6,755,812 B2 | 6/2004 | Peterson et al. |
| 6,761,696 B1 | 7/2004 | Wong |
| 6,837,890 B1 | 1/2005 | Chludzinski et al. |
| 6,860,876 B2 | 3/2005 | Chen |
| 6,997,908 B2 | 2/2006 | Carrillo, Jr. et al. |
| 7,169,162 B2 | 1/2007 | Garakani |
| 7,232,452 B2 | 6/2007 | Adams et al. |
| 7,294,124 B2 | 11/2007 | Eidenschink |
| 7,374,560 B2 | 5/2008 | Ressemann et al. |
| 7,422,579 B2 | 9/2008 | Wahr et al. |
| 7,544,201 B2 | 6/2009 | Pepper |
| 7,604,612 B2 | 10/2009 | Ressemann et al. |
| 7,697,996 B2 | 4/2010 | Manning et al. |
| 7,717,899 B2 | 5/2010 | Bowe et al. |
| 7,736,355 B2 | 6/2010 | Itou et al. |
| 7,762,984 B2 | 7/2010 | Kumoyama et al. |
| 7,763,012 B2 | 7/2010 | Petrick et al. |
| 7,959,603 B2 | 6/2011 | Wahr et al. |
| 8,048,032 B2 | 11/2011 | Root et al. |
| 8,142,413 B2 | 3/2012 | Root et al. |
| 8,142,468 B2 * | 3/2012 | Inderbitzen ....... A61M 25/0141 604/165.02 |
| 8,292,850 B2 | 10/2012 | Root et al. |
| 8,292,872 B2 | 10/2012 | Soetermans |
| 8,613,722 B2 | 12/2013 | Lee et al. |
| 8,684,917 B2 * | 4/2014 | Rosenschein ......... A61M 25/09 600/200 |
| 8,721,624 B2 | 5/2014 | Wilson et al. |
| 8,814,890 B2 | 8/2014 | Miyata et al. |
| RE45,380 E | 2/2015 | Root et al. |
| 8,996,095 B2 | 3/2015 | Anderson et al. |
| 9,144,662 B2 | 9/2015 | Caprio et al. |

(56) References Cited

U.S. PATENT DOCUMENTS

| | | | |
|---|---|---|---|
| RE45,760 E | 10/2015 | Root et al. | |
| RE45,776 E | 10/2015 | Root et al. | |
| 9,149,173 B2* | 10/2015 | Scopton | A61B 1/018 |
| 9,211,390 B2* | 12/2015 | Conklin | A61L 31/14 |
| RE46,116 E | 8/2016 | Root et al. | |
| 10,080,874 B2* | 9/2018 | Fuller | A61M 25/10 |
| 10,173,029 B2 | 1/2019 | Webster et al. | |
| RE47,379 E | 5/2019 | Root et al. | |
| 10,390,983 B2* | 8/2019 | Nakaya | A61F 2/966 |
| 10,668,254 B2* | 6/2020 | Daniels | A61M 25/1011 |
| 10,751,514 B2 | 8/2020 | Brenizer et al. | |
| 10,946,177 B2* | 3/2021 | Peterson | A61M 25/0043 |
| 10,974,028 B2 | 4/2021 | Buller et al. | |
| 11,712,544 B2 | 8/2023 | Brenizer et al. | |
| 11,813,420 B2* | 11/2023 | Wisman | A61M 25/09 |
| 11,857,743 B2* | 1/2024 | Fantuzzi | A61M 25/00 |
| 2001/0016712 A1 | 8/2001 | Hamilton | |
| 2002/0165598 A1 | 11/2002 | Wahr et al. | |
| 2003/0114732 A1* | 6/2003 | Webler | A61B 1/00096 600/121 |
| 2003/0195546 A1 | 10/2003 | Solar et al. | |
| 2003/0233117 A1 | 12/2003 | Adams et al. | |
| 2004/0010280 A1 | 1/2004 | Adams et al. | |
| 2004/0087933 A1 | 5/2004 | Lee et al. | |
| 2004/0127927 A1 | 7/2004 | Adams | |
| 2004/0236215 A1 | 11/2004 | Mihara et al. | |
| 2005/0004523 A1 | 1/2005 | Osborne et al. | |
| 2005/0015073 A1 | 1/2005 | Kataishi et al. | |
| 2005/0182437 A1 | 8/2005 | Bonnette et al. | |
| 2006/0135948 A1* | 6/2006 | Varma | A61M 25/09041 604/523 |
| 2006/0247661 A1 | 11/2006 | Richards et al. | |
| 2007/0260219 A1 | 11/2007 | Root et al. | |
| 2008/0082045 A1 | 4/2008 | Goldfarb et al. | |
| 2008/0243171 A1 | 10/2008 | Ressemann et al. | |
| 2009/0005755 A1 | 1/2009 | Keith et al. | |
| 2009/0264865 A1 | 10/2009 | Kawai | |
| 2013/0072904 A1 | 3/2013 | Musbach et al. | |
| 2013/0116701 A1 | 5/2013 | Wang et al. | |
| 2013/0197483 A1 | 8/2013 | Anderson et al. | |
| 2014/0012281 A1 | 1/2014 | Wang et al. | |
| 2014/0018773 A1 | 1/2014 | Wang et al. | |
| 2014/0025004 A1 | 1/2014 | Falk et al. | |
| 2014/0025043 A1 | 1/2014 | Wang et al. | |
| 2014/0039461 A1 | 2/2014 | Anderson et al. | |
| 2014/0052097 A1 | 2/2014 | Petersen et al. | |
| 2014/0081243 A1 | 3/2014 | Zhou et al. | |
| 2014/0142506 A1 | 5/2014 | Prindle et al. | |
| 2014/0171914 A1 | 6/2014 | Rowe et al. | |
| 2014/0249508 A1 | 9/2014 | Wang et al. | |
| 2014/0276618 A1 | 9/2014 | Di Caprio et al. | |
| 2014/0358123 A1 | 12/2014 | Ueda et al. | |
| 2015/0051633 A1 | 2/2015 | Sina | |
| 2015/0151090 A1 | 6/2015 | Sutton et al. | |
| 2015/0190615 A1* | 7/2015 | Shaltis | A61M 25/0147 604/95.04 |
| 2015/0282821 A1 | 10/2015 | Look et al. | |
| 2016/0121080 A1 | 5/2016 | Cottone | |
| 2016/0346515 A1 | 12/2016 | Buller et al. | |
| 2018/0161547 A1 | 6/2018 | Brenizer et al. | |
| 2021/0008342 A1 | 1/2021 | Buller et al. | |
| 2021/0008343 A1 | 1/2021 | Brenizer et al. | |
| 2021/0008355 A1 | 1/2021 | Peterson et al. | |
| 2022/0313950 A1 | 10/2022 | Brenizer et al. | |
| 2024/0189547 A1 | 6/2024 | Brenizer et al. | |

FOREIGN PATENT DOCUMENTS

| | | |
|---|---|---|
| EP | 0313558 B1 | 1/1991 |
| EP | 0380873 B1 | 5/1994 |
| EP | 0365993 B1 | 12/1994 |
| EP | 0881921 A1 | 12/1998 |
| EP | 1084728 A1 | 3/2001 |
| EP | 0992260 B1 | 9/2007 |
| JP | H10507095 A | 7/1998 |
| JP | 2004275435 A | 10/2004 |
| JP | 2012135379 A | 7/2012 |
| WO | 1984003633 A1 | 9/1984 |
| WO | 1996001604 A1 | 1/1996 |
| WO | 1997037713 A1 | 10/1997 |
| WO | 2000024451 A9 | 11/2000 |
| WO | 2014028898 A2 | 2/2014 |
| WO | 2016191415 A1 | 12/2016 |
| WO | 2017019900 A1 | 2/2017 |

OTHER PUBLICATIONS

Bonzel, T. et al. "The Sliding Rail System (Monorail): Description of a New Technique for Intravascular Instrumentation and its Application to Coronary Angioplasty," Z. Kardiol. 76, Supp. 6 (1987), pp. 119-122.

EP search report mailed Apr. 16, 2018, in European Application No. 17193571.1 filed Sep. 27, 2017.

Iqbal et al. "Coronary stents: historical development, current status and future directions," British Medical Bulletin, 2013, 106: 193-211.

Japanese Office Action mailed Jan. 29, 2018, in Japanese Application No. 2017-542898.

PCT International Search Report mailed Sep. 1, 2016 in connection with PCT Application No. PCT/US2016/033904 filed May 24, 2016.

PCT International Search Report mailed Apr. 29, 2019, in PCT application No. PCT/US2019/016235.

PCT Written Opinion mailed Sep. 1, 2016 in connection with PCT Application No. PCT/US2016/033904 filed May 24, 2016.

Takahashi, Saeko. "New Method to Increase a Backup Support of a 6 French Guiding Coronary Catheter," Catheterization and Cardiovascular Interventions 63:452-456 (2004), 5 pages, published online in Wiley InterScience (www.interscience.wiley.com).

Topol, Eric J. "Textbook of Interventional Cardiology," Saunders Elseveir, 5th Edition, 2008, p. 277-280.

Tully, Shawn. "Blood Feud This little piece of metal is worth $4.5 billion this year, generates more profits than a blockbuster drug, and has sparked one of the weirdest corporate battles ever. It could also save your life." CNN Money, May 31, 2004, 5 pages. Retrieved Jan. 14, 2019 on the Internet: https://money.cnn.com/magazines/fortune/fortune_archive/2004/05/31/370693/index.htm.

Vascular Solutions, Inc. "GuideLiner V3 catheter: Guide Extension Catheter with Half-Pipe Technology" [Brochure], Dec. 2013, Minneapolis, MN.

* cited by examiner

GUIDEWIRE FIXATION

CLAIM OF PRIORITY

This patent application is a continuation application of non-provisional patent application Ser. No. 15/163,044, now U.S. Pat. No. 10,974,028, entitled "GUIDEWIRE FIXATION" and filed May 24, 2016, and which claims the benefit of priority under 35 U.S.C. § 119(e) to U.S. Provisional Patent Application Ser. No. 62/166,259, entitled "GUIDEWIRE FIXATION" and filed on May 26, 2015, and to U.S. Provisional Patent Application Ser. No. 62/190,879, entitled "GUIDEWIRE FIXATION" and filed on Jul. 10, 2015, each of which is herein incorporated by reference in its entirety.

TECHNICAL FIELD

This patent document relates to medical devices. More particularly, but not by way of limitation, the patent document relates to percutaneous devices and methods suitable for use in minimally invasive treatment of various disorders and diseases.

BACKGROUND

Minimally invasive medicine and the practice of gaining access into a blood vessel or other hollow bodily structure to facilitate the subsequent introduction and placement of catheters or other interventional medical devices has been evolving since creation of the Seldinger technique in the early 1950s.

An important advance during this evolution was gaining the ability to exchange catheters or other interventional medical devices over a single indwelling guidewire without displacing the guidewire proximally, which surrenders access to a desired diseased site, or distally, which risks perforation or other guidewire-induced patient injury. This "over-the-wire" (OTW) or "long wire" exchange technique requires a long guidewire length so that the guidewire can be handled and stabilized from outside a patient's body at all times during a procedure. The portion of the guidewire extending out of the patient must be at least slightly longer than the full-length lumen of the catheter (or other interventional medical device) to be employed. In this way, a proximal end of the guidewire can protrude from a proximal end of the catheter and can be held by an operating physician or his/her assistant to maintain the guidewire's indwelling positioning.

To exchange one catheter for another using the OTW technique, the physician and assistant must make a series of well-coordinated, one-to-one movements between the guidewire and each catheter. The assistant pushes the guidewire the same amount as the physician pulls back on a first catheter until the first catheter is completely outside of the patient and the physician gains control over the guidewire at its entry site into the patient. The assistant then pulls the first catheter off the guidewire and backloads a second catheter over the guidewire and into the patient to perform a second operation, requiring this same push-pull technique in reverse. Once the second catheter is fully loaded onto the guidewire, the guidewire's proximal end can protrude from the catheter's proximal end and can be held by the assistant, typically standing well apart from the physician. These exchange maneuvers must be guided fluoroscopically to monitor distal guidewire position, thereby increasing the dose of radiation to which the patient, physician and assistant are exposed during the procedure. Moreover, these exchange maneuvers are prone to error resulting in loss of indwelling guidewire position.

A technique that allows for a much shorter guidewire length to be used and more physician control over the guidewire was developed to simplify catheter exchanges. Known as the "rapid exchange," "monorail," or "short wire" technique, it is used in conjunction with rapid exchange, monorail or short wire catheters, which include a shortened guidewire passageway extending along only a portion of a catheter's length. The rapid exchange technique differs from the OTW technique in that a guidewire is fed into the shortened passageway and exits at a point between the catheter's distal and proximal ends via a port or channel formed in the side of the catheter. The physician can perform a short wire catheter exchange by handling a guidewire portion length slightly longer than a length of the shortened passageway (instead of a guidewire length slightly longer than an entire catheter, as is the case when using the OTW technique). This facilitates the physician maintaining control of the guidewire at all times and reduces the need for coordinating x-ray guided push-pull exchange movements with an assistant.

OVERVIEW

As vascular interventions grow in complexity, there are an increasing number of special-purpose OTW catheters embodying full-length guidewire lumens; however, physicians generally prefer the convenience of using a short rapid exchange length guidewire versus the more cumbersome OTW length guidewire.

The present inventors recognize that when OTW catheters are used in combination with rapid exchange length guidewires, an operating physician is unable to maintain a hold onto the guidewire during an entire catheter exchange process. When the guidewire can no longer be held, guidewire position can easily be lost as the OTW catheter pulls the guidewire back with it while being withdrawn. In a similarly undesirable manner, when trying to advance the OTW catheter over the rapid exchange guidewire, the guidewire can be unintentionally pushed distally by the catheter during the time when the guidewire's proximal end cannot be held and stabilized by the physician or his/her assistant. This advancement of the guidewire poses a potential risk of vessel perforation or other damage, because the guidewire's distal tip can advance into a small or diseased vessel that the physician does not intend to cannulate. Alternatively, redundant loops of guidewire can form in front of the OTW catheter being advanced leading to loss of wire control and positioning. Any of these uncontrolled guidewire movements arising from OTW catheter movements over rapid exchange length guidewires can lead to procedural inefficiency, procedural failure and/or patient complications.

The present inventors further recognize that devices and methods to fix indwelling guidewire positioning during percutaneous procedures are needed, particularly when the use of an OTW catheter and a rapid exchange length guidewire are anticipated. The present devices and methods include means to engage an intermediate or distal end portion of a guidewire against an inner surface of a tubular member. Once the guidewire position is locked by its engagement against the tubular member's inner surface, withdrawal of a first OTW catheter and subsequent introduction of a second OTW catheter over the guidewire is possible without moving the guidewire longitudinally relative to the tubular member.

A percutaneous device for use with a guide catheter and a guidewire, particularly a rapid exchange length guidewire, can comprise a relatively flexible elongate tube member, a push member, and a fixation mechanism such as a fixation balloon. The tube member can define a lumen sized and shaped to receive one or more interventional medical devices and can have an outer diameter smaller than a lumen of the guide catheter. In this way, a portion of the tube member can extend within and beyond a distal end of the guide catheter to facilitate deeper delivery of the one or more interventional medical devices into a desired target vessel or other hollow structure. The push member can be attached to the tube member and can extend proximally therefrom for slidably positioning the tube member relative to the guide catheter. The push member can include a lumen in fluid communication with an interior of the fixation balloon for delivering inflation fluid to, or removing fluid from, the balloon. The fixation balloon can be positioned on a portion of the push member—proximal to or within the tube member—and can include a size and shape to engage or lock the guidewire against an inner surface of the guide catheter or the tube member when inflated. This engagement or locking can facilitate the exchange of an OTW catheter while maintaining the position of the guidewire within the desired target vessel or other hollow structure.

A method of inserting an OTW catheter or other interventional medical device into a patient using an in situ rapid exchange length guidewire as a rail can comprise advancing a distal end of a guide catheter over the guidewire to a position adjacent an ostium of a desired vessel or other hollow structure. A percutaneous device comprising a push member, a relatively flexible elongate tube member, and a fixation mechanism such as a fixation balloon can be advanced into the guide catheter and over the guidewire. The tube member can be positioned in coaxial alignment with the guide catheter with its distal end portion extending beyond the distal end of the guide catheter. Longitudinal movement of the guidewire relative to the guide catheter or the tube member can be inhibited by inflating the fixation balloon, thereby engaging the guidewire against an inner surface of the guide catheter or the tube member. After inflating the fixation balloon, the OTW catheter can be loaded onto a proximal end of the locked guidewire and advanced distally to a location proximal of the fixation balloon. When the proximal end of the guidewire becomes accessible outside of a proximal end of the OTW catheter, a physician can grasp the proximal end of the guidewire and the fixation balloon can then be deflated so that the OTW catheter can be further advanced into the desired vessel or other hollow structure.

These and other examples and features of the present devices and methods will be set forth, at least in part, in the following Detailed Description. This Overview is intended to provide non-limiting examples of the present subject matter—it is not intended to provide an exclusive or exhaustive explanation. The Detailed Description below is included to provide further information about the present devices and methods.

BRIEF DESCRIPTION OF THE DRAWINGS

In the drawings, like numerals can be used to describe similar features and components throughout the several views. The drawings illustrate generally, by way of example, but not by way of limitation, various device and method embodiments discussed in this patent document.

The drawings are not necessarily to scale. Certain features and components may be shown exaggerated in scale or in schematic form, and some details may not be shown in the interest of clarity and conciseness.

DETAILED DESCRIPTION

Oftentimes, after a catheter or other interventional medical device is inserted into a patient, it can be necessary to withdraw the catheter or device to substitute an alternate-sized catheter or device. For example, the profile of a deflated balloon of a dilatation catheter can sometimes be too large to fit through a diseased site (e.g., a stenosis) to be treated, or the balloon profile may be so small that, upon inflation of the balloon, the diseased site is not sufficiently dilated. When this occurs, the dilatation balloon catheter needs to be exchanged for one of a different (smaller or larger) size, so that the diseased site can be crossed and properly treated upon inflation of the balloon. The catheter or device may also or alternatively have poor control or low flexibility resulting in an inability to track to an anatomic landmark distal to the diseased site. In this case, the catheter or device must be exchanged for one with better tracking characteristics so that the anatomic landmark can be reached. These substitutions are completed during a catheter or device exchange.

The present percutaneous devices and methods allow for reliable insertion and removal of both OTW and rapid exchange catheters or other interventional medical devices over a guidewire of any length (including rapid exchange guidewires having a length of about 190 centimeters (cm) or less), while maintaining the position of the guidewire relative to a tubular member or an anatomic landmark within vasculature. Maintaining the indwelling position of the guidewire during such interventional medical device insertions and removals reduces the need for coordinating x-ray guided push-pull exchange movements as would otherwise be required.

It is believed that the present devices and methods will find great utility by interventional cardiologists performing percutaneous coronary interventions with rapid exchange length guidewires, particularly when an OTW catheter is employed or anticipated. The present devices and methods can also allow for maintaining a position of the guide catheter relative to an ostium of a target vessel or other hollow structure in which the anatomic landmark is located through utilization of the deep vessel seatability of its tube member. Although the remainder of this patent document generally discusses and illustrates use of the present devices and methods with reference to treating coronary vessels, it should be understood that the devices and methods can also be used for treating other diseased or blocked vessels or other hollow structures (e.g., biliary tract, ureter, etc.) throughout a patient's body where guidewires are employed.

Figure 1:
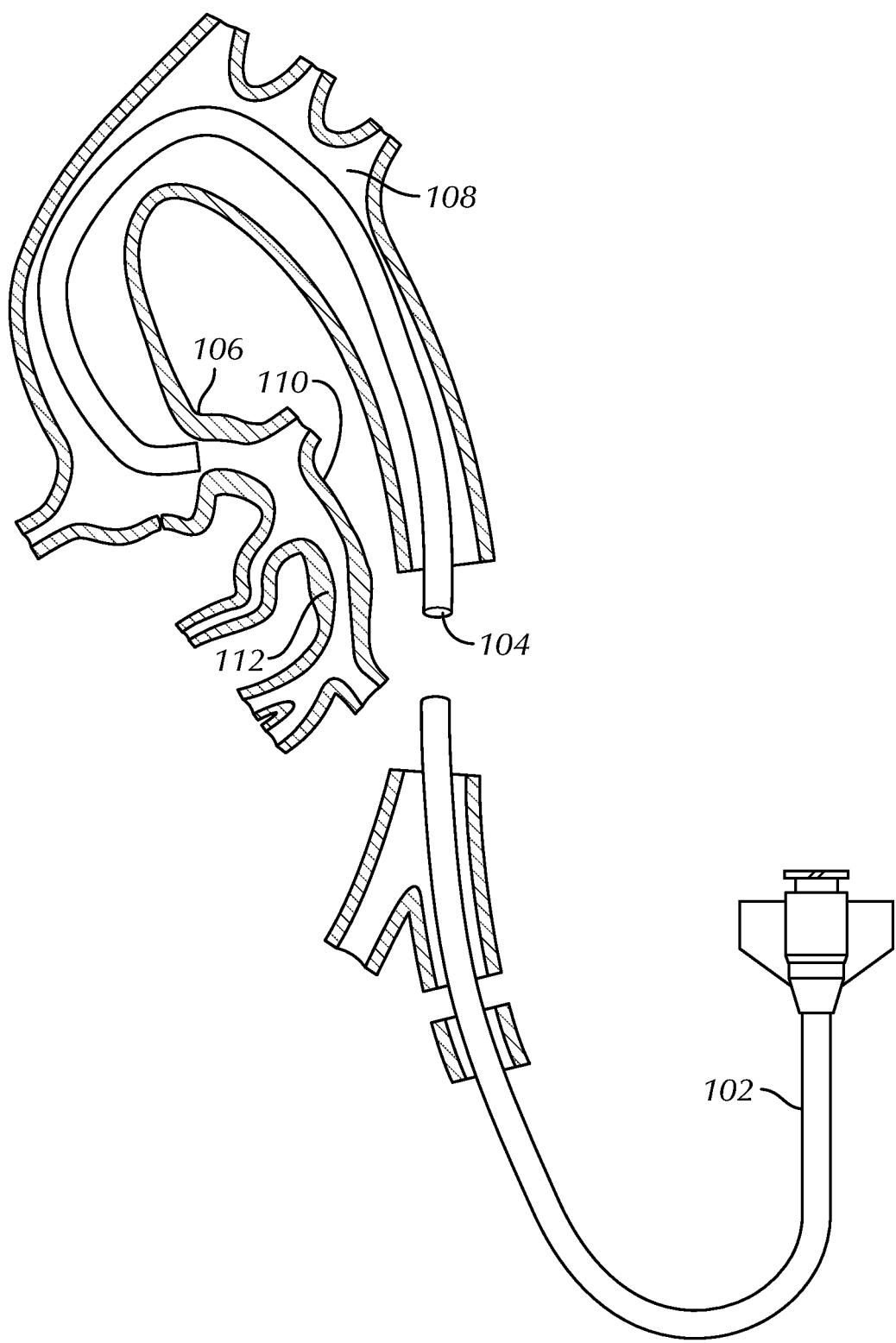
FIG. 1 illustrates a plan view of a guide catheter advanced through an aorta to an ostium of a coronary artery, as constructed in accordance with at least one embodiment.

Minimally-invasive cardiac interventions, such as percutaneous transluminal coronary angioplasty procedures, are utilized throughout the world and typically include the use a guide catheter 102, as illustrated in FIG. 1. The guide catheter 102 is an elongate tubular member defining a guide catheter lumen 104 throughout its length. The guide catheter 102 can be formed of polyurethane, for example, and can be shaped to facilitate its passage to a coronary ostium 106 or other region of interest within a patient's body. In the example of FIG. 1, a 6 French (F), 7 F or 8 F guide catheter 102 can be inserted at a femoral artery and advanced through the aorta 108 to a position adjacent to the ostium 106 of a coronary artery 110. The diameter and rigidity of the guide catheter 102 oftentimes does not permit it to be advanced beyond the ostium 106 into the coronary artery 110 requiring treatment, and thus, a dilatation balloon catheter must be advanced independently of the guide catheter 102 to reach a diseased site 112.

Maintaining the position of the guide catheter's 102 distal end at the ostium 106 can be desirable to facilitate the dilatation balloon catheter successfully reaching the diseased site 112. When resistance is encountered as attempts are made to deliver the dilatation balloon catheter, the guide catheter 102 can back-out or withdraw from the ostium 106. A heart's intrinsic beat can also cause the guide catheter's 102 distal end to lose its positioning or otherwise be shifted so that it no longer is positioned to guide the dilatation balloon catheter to the diseased site 112. Because of this shift away from the ostium 106, access to the coronary artery 110 and the diseased site 112 can require repeated repositioning of the guide catheter 102 in order to bring its distal end back into engagement with the ostium 106.

Figure 2:
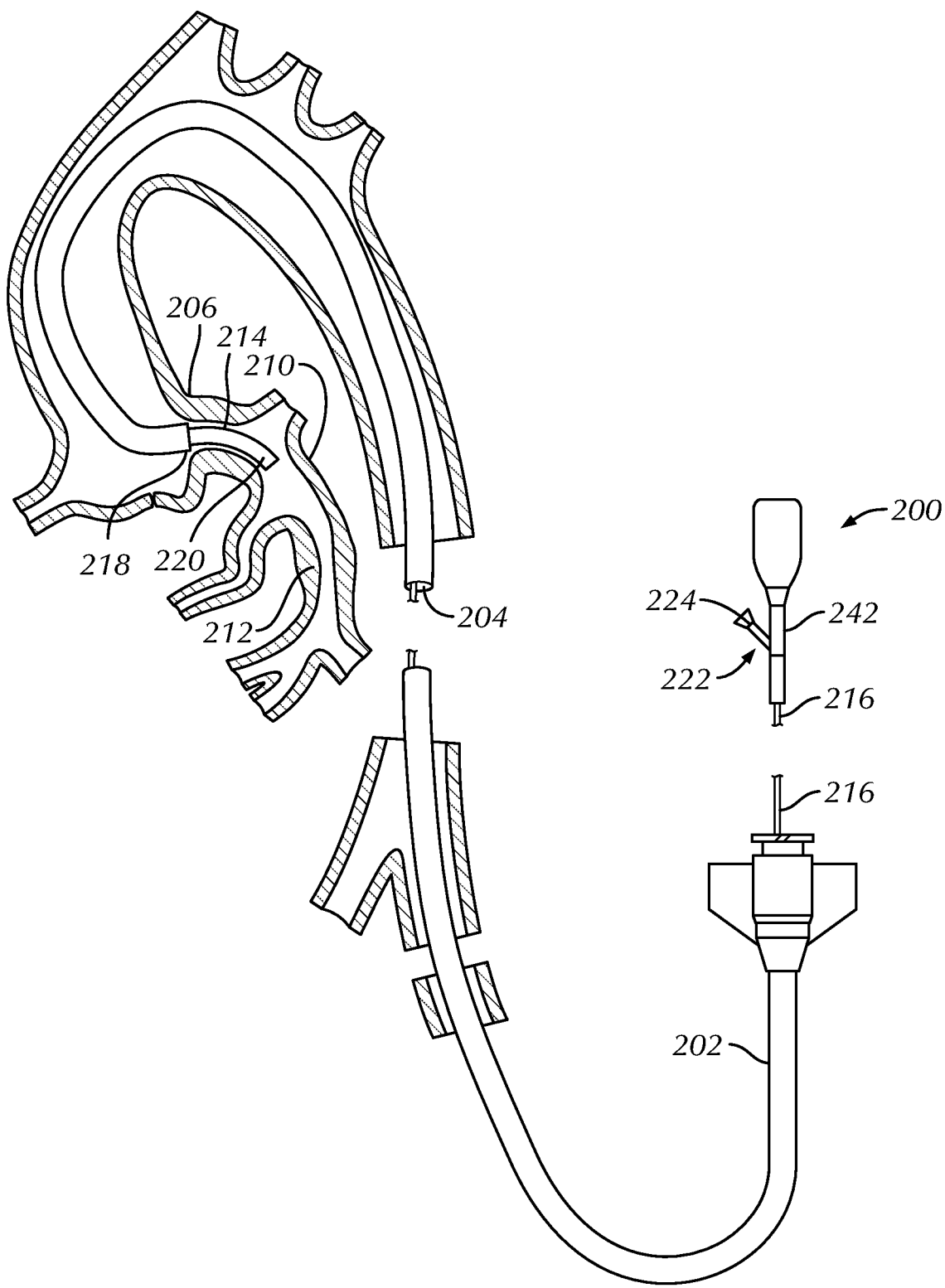
FIG. 2 illustrates a plan view of a percutaneous device used in conjunction with a guide catheter, as constructed in accordance with at least one embodiment.
Figure 3:
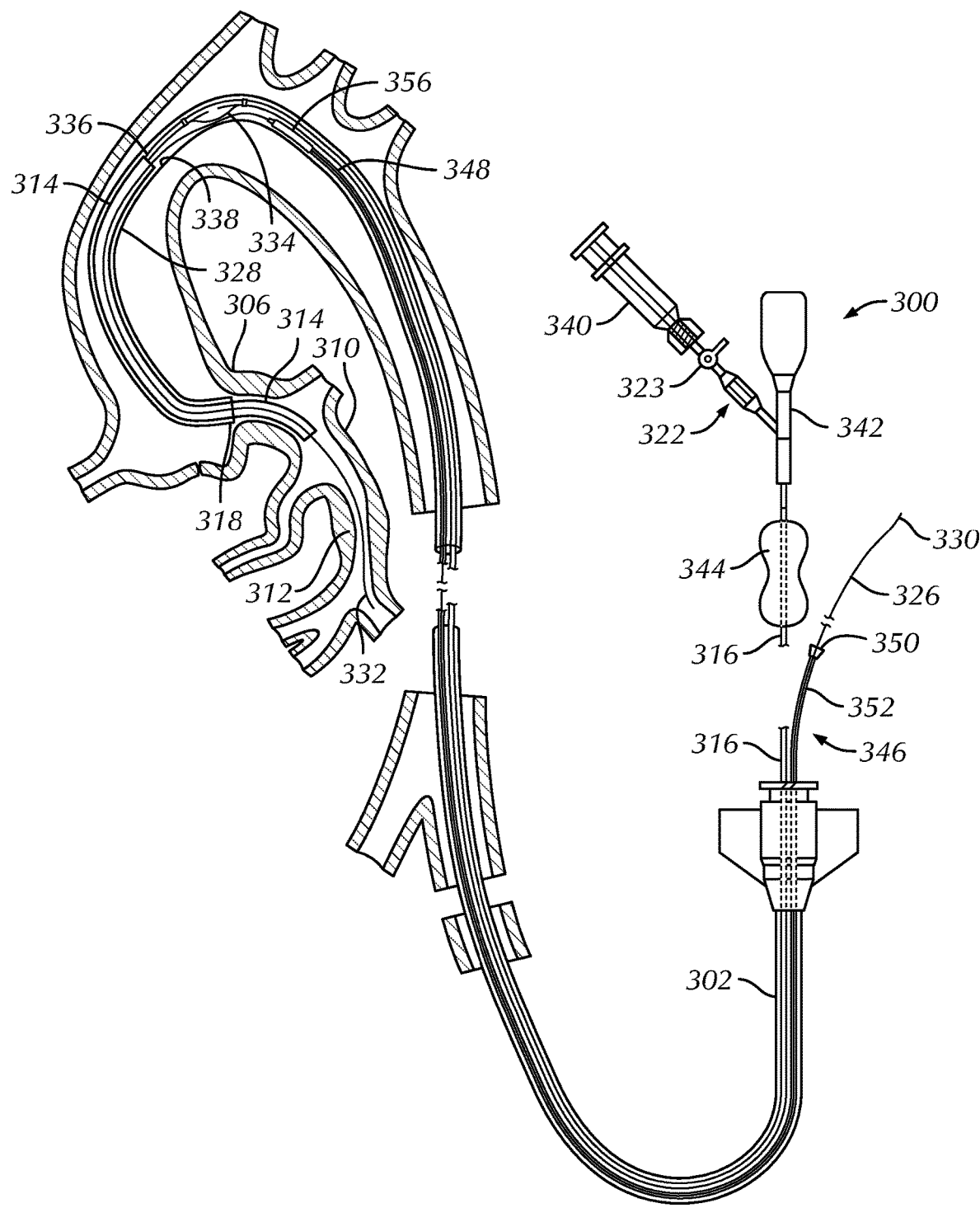
FIG. 3 illustrates an exposed view of a percutaneous device used in conjunction with a guide catheter and a guidewire, as constructed in accordance with at least one embodiment.

The present percutaneous device 200 can improve access to a coronary artery 210 and an anatomic landmark, which is typically positioned distal to a diseased site 212, and includes a relatively flexible elongate tube member 214, a push member 216, and a fixation mechanism (e.g., the fixation balloon illustrated in FIG. 3). FIG. 2 illustrates a portion of the tube member 214 extending through a guide catheter 202 and beyond its distal end 218 into the coronary artery 210. By extending into the coronary artery 210, the tube member 214 can stabilize the positioning of the guide catheter 202 relative to the artery's ostium 206 and can allow for improved access to the diseased site 212 where a dilatation balloon catheter can be used to perform an appropriate intervention. The tube member 214 can define a lumen 220 to receive the dilatation balloon catheter and can have an outer diameter smaller than a lumen 204 of the guide catheter 202.

The push member 216 can be attached at least to a proximal end of the tube member 214 and extends proximally from this attachment so that its proximal end portion 242 is accessible to an operating physician outside of a patient's body. The push member 216 allows the physician to position the tube member 214 between a first position, in which the tube member 214 is entirely positioned within the guide catheter 202, and the illustrated second extended position, in which a portion of the tube member 214 extends beyond the distal end 218 of the guide catheter 202. In varying examples, the push member 216 can include a hypotube having the ability to delivery inflation fluid to, or remove fluid from, the fixation balloon (FIG. 3) and its proximal end portion 242 can include an inflation manifold 222 couplable to an inflation device, such as by a luer fitting 224.

With distal end portions of a guide catheter 302 and a percutaneous device 300 in position adjacent an ostium 306 and within a coronary artery 310, respectively, an in situ guidewire 326 (e.g., a rapid exchange length guidewire) can lie freely therein and can be rotated and controlled from its proximal end 330, as illustrated in FIG. 3. For anatomical orientation and relative positioning, doses of contrast medium can be supplied through the guide catheter 302 and a tube member 314 of the percutaneous device 300. When the guidewire 326 has crossed a diseased site 312 in the coronary artery 310 to be treated, its distal tip 332 can be positioned on the site's far side adjacent to an anatomic landmark.

Next, a fixation mechanism of the percutaneous device 300 can be increased in size to engage the guidewire 326 against an inner surface 338 of an intermediate or distal end portion 328 of the guide catheter 302. The fixation mechanism can take various forms including, for example, expandable, extendible or resilient arms, fingers, latches or inflatable members. As illustrated in the example of FIG. 3, the fixation mechanism can be a fixation balloon 334 positioned on a distal end portion 336 of a push member 316, proximal to the tube member 314, and can include an inflated size and shape to engage the guidewire 326 against the inner surface 338 of the intermediate or distal end portion 328 of the guide catheter 302. Inflation of the fixation balloon 334 can inhibit longitudinal movement of the guidewire 326 relative to the guide catheter 302, the tube member 314, or the anatomic landmark with adequate force for an OTW catheter or other interventional medical device to be advanced or withdrawn without causing guidewire 326 movements. Adequate force to secure a 0.014 inch (in) (0.0356 cm) guidewire is believed to be about 30 grams (g) to 60 g based on clinical bench testing.

The fixation balloon 334 or other fixation mechanism can alternatively be positioned within the tube member 314 and can include an enlarged size and/or shape to engage the guidewire 326 against an inner surface of the tube member 314. This fixation balloon 334 position provides direct and local control over the position of the guidewire 326 near its distal end portion.

Inflation of the fixation balloon 334 can be completed by connecting the tip of a syringe or dedicated inflation device 340 into an inflation manifold 322, which is coupled to a proximal end portion 342 of the push member 316. By depressing a plunger of the syringe 340, inflation fluid or gas can be urged through a lumen of the push member 316 to the fixation balloon 334. The inflation fluid typically includes a sterile saline solution or a sterile solution consisting of saline and contrast media. The contrast media solution can be used when it is desirable to view the fixation balloon 334 expansion using fluoroscopy. Once fluid has been urged into the fixation balloon 334 and the tip of the syringe is withdrawn from the inflation manifold 322, a valve within the manifold or a stop cock 323 can close or be closed to maintain the balloon 334 in an inflated state.

Optionally, the percutaneous device 300 can further include an inflation indicator bulb 344 positioned on the proximal end portion 342 of the push member 316. The indicator bulb 344 can be in fluid communication with the interior of the fixation balloon 334 and can provide an external (outside the patient's body) indication to the operating physician of the inflation status of the fixation balloon 334.

After using the fixation balloon 334 to engage the guidewire 326 against the inner surface 338 of the distal end portion 328 of the guide catheter 302, for example, the proximal end 330 of the guidewire 326 can be introduced into an OTW dilatation balloon catheter 346, for example, using a backloading technique. In the absence of a torquer on the guidewire 326, the proximal end 330 of the guidewire 326 can be inserted in a rearward direction through the tip and an axial lumen of the dilatation balloon catheter 346. The guidewire 326 can be advanced rearward by holding a distal end portion 348 of the dilatation balloon catheter 346 in one hand and advancing the guidewire 326 rearward with the other hand. As the dilation catheter 346 is distally advanced into the coronary artery 310, the proximal end 330 of the guidewire 326 exits through an opening 350 at a proximal end portion 352 of the catheter and can be grasped by the physician.

The fixation balloon 334 can then be deflated, freeing the guidewire 326 from its captive or fixed-position state relative to the guide catheter 302 or the anatomic landmark. The dilatation balloon catheter 346 can then be further advanced distally along the guidewire 326, past the distal end 318 of the guide catheter 302 and the tube member 314, and through the coronary artery 310 to the anatomic landmark. This occurs while the proximal end 330 of the guidewire 326 extends out of the proximal end portion 352 of the dilatation balloon catheter 346 and is held by the physician to prevent its advancement within the coronary artery 310. A balloon 356 of the dilatation balloon catheter 346 can be positioned across the diseased site 312 so that, upon its inflation, the diseased site 312 is dilated.

Figure 4:
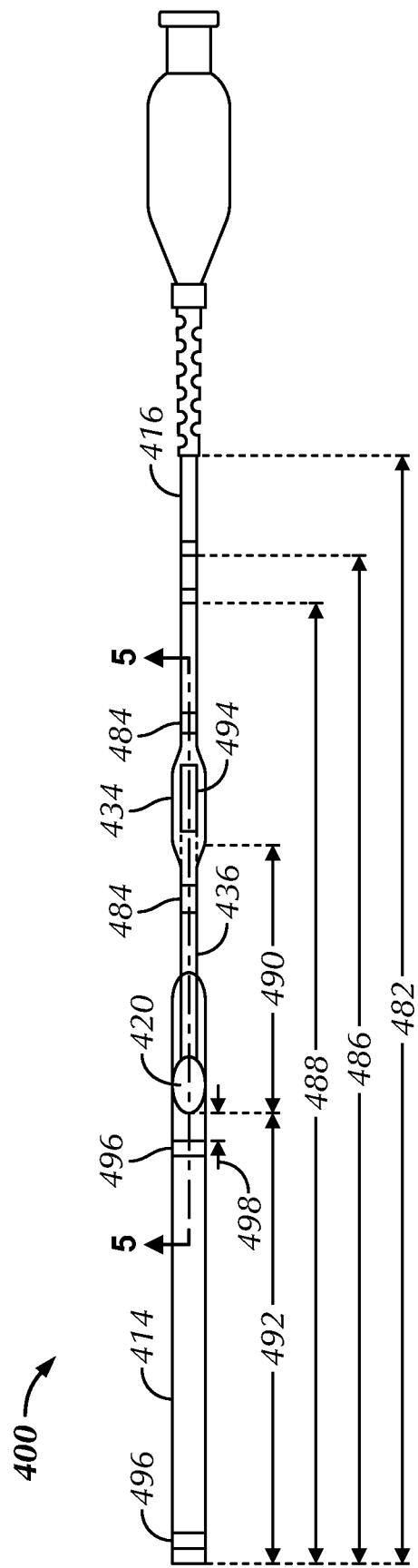
FIG. 4 illustrates an elevational view of a percutaneous device, as constructed in accordance with at least one embodiment.

FIG. 4 illustrates an elevational view of an example percutaneous device 400 for use with a guide catheter and a guidewire. The percutaneous device 400 can include a relatively flexible elongate tube member 414, a push member 416 and a fixation balloon 434, and can have a collective length 482 of 120 cm-180 cm, for example.

Markers on the percutaneous device 400 can allow an operating physician to identify positioning of the device's components relative to patient anatomy, the guide catheter, and any international medical devices used during a procedure. For example, one or more depth markers 484 can be printed on the push member 416 and can be positioned at first 486 (e.g., about 105 cm) and second 488 (e.g., about 95 cm) lengths from a distal end of the tube member 414. A radiopaque marker 494 can be positioned within the fixation balloon 434 and can be formed by gold plating around a portion of the push member 416. And one or more radiopaque marker bands 496 can be positioned on the tube member 414 and can be composed of tungsten, platinum or an alloy thereof. A first marker band 496 can be positioned at a length 498 slightly distal (e.g., about 4 millimeters (mm) distal) to a fully-round entrance of the tube member 414 and a second marker band 496 can be positioned near the tube member's distal end.

The fixation balloon 434 can be positioned on a distal end portion 436 of the push member 416, such as at a length 490 proximal (e.g., about 5 cm proximal) to the fully-round entrance of the tube member 414.

The tube member 414 can extend for a length 492 of about 6 cm-30 cm and can define a lumen 420. The lumen 420 can be larger than an outer diameter of the push member 416 and within one or two French sizes of an inner diameter of the guide catheter so as to allow dilatation balloon catheters, stents and other interventional medical devices to pass through.

Figure 5:
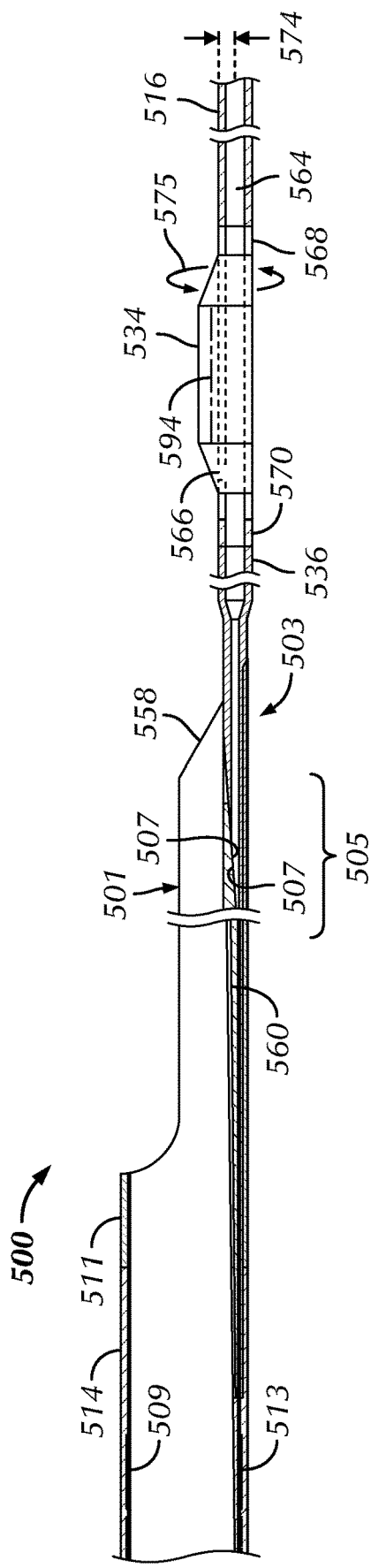
FIG. 5 illustrates a side cross-sectional view of a percutaneous device, such as along line 5-5 of the example of FIG. 4.

FIG. 5 illustrates a side cross-sectional view of a percutaneous device 500, such as along line 5-5 of FIG. 4. Describing this illustration in a proximal-to-distal direction, a push member 516 can define or otherwise include a lumen 564. The lumen 564 can be in fluid communication with an interior of a fixation balloon 534 for the delivery of inflation fluid to, or removal of fluid from, the balloon. In varying examples, the push member 516 can include a hypotube having a port 566 in its sidewall to fluidly couple the lumen 564 and the fixation balloon 534. The lumen 564 can be plugged or otherwise sealed distal to the fixation balloon 534 to form a closed inflation system.

The fixation balloon 534 can be positioned on a distal end portion 536 of the push member 516, proximal to a tube member 514, and wrapped about the port 566. The fixation balloon 534 can be laser welded or otherwise bonded to the push member 516 at a proximal annular bond 568 and a distal annular bond 570. A center of the fixation balloon 534 can be offset vertically 574 and/or radially 575 relative to axial (horizontal and vertical) center planes of the push member 516. The radial offset 575 can help the balloon avoid inhibiting delivery of interventional medical devices into the tube member 514, while the vertical offset 574 can effectively urge a guidewire against an inner surface of a guide catheter when inflated, for example. In varying examples, the fixation balloon 534 has an inflated outer diameter slightly larger than an inner diameter of the guide catheter in which the percutaneous device 500 is being utilized. The fixation balloon 534 can have an effective locking length of about 10-12 mm and a marker 594 can extend along a portion of this effective length.

The fixation balloon 534 can include one or multiple polymer layers. In an example, the fixation balloon 534 includes a single polymer layer formed of nylon, polyether block amides, polyethylene terephthalate (PET) or polyurethane. In another example, the fixation balloon 534 includes an inner polymer layer and an outer polymer layer; the inner polymer layer can include a high durometer polymer to increase resistance to bursting and provide enhanced outward force, and the outer polymer layer can include a lower durometer polymer providing flexibility and conformance with a vessel wall.

A proximal end portion 558 of the tube member 514 can be coupled to the distal end portion 536 of the push member 516. The arrangement or configuration of this coupling can vary. For example, the tube member 514 can have an opening formed in its wall and the push member 516 can be disposed within the opening. Inserting the push member 516 into the opening can result in a mechanical coupling between the members and additional or alternative bonds (e.g., adhesive bonds, thermal bonds, welds, brazes, etc.) can be utilized. The distal end portion 536 of the push member 516 can be flattened to provide a larger surface area to secure to the tube member 514. Coupling mechanisms facilitated by a third component (e.g., a metal or polymer collar or concave track) bonded between or integrated with the proximal end portion 558 of the tube member 514 and the distal end portion 536 of the push member 516 are also contemplated. Polymers forming the third component can become less stiff and more flexible in a proximal-to-distal direction to provide a gradual flexibility transition between the more rigid push member 516 and the more flexible tube member 514.

In the example shown, the proximal end portion 558 of the tube member 514 includes a concave track 501 that is accessible from a longitudinal side defined transverse to a longitudinal axis of the tube member 514. This concave track 501 provides a larger area to receive a dilatation balloon catheter, stent or other interventional medical device into the tube member 514 than an area associated with an opening oriented perpendicular to the longitudinal axis of the tube member. A backbone support structure 503 of this concave track 501 can transition from the push member 516, in the form of a relatively rigid hypotube, to a lumen-less, more flexible structure 560 that is embedded in the tube member 514. The distal end portion 536 of the hypotube 516 can have an outer diameter that gradually reduces in the direction of its distal end, where it can be welded to a metallic (e.g., stainless steel) ribbon member 560 that can also gradually reduce in size in the direction of its distal end. At a welded region 505 between the distal end of the hypotube 516 and the proximal end of the metallic ribbon 560, each component can be cut at mating angles 507 to provide a controlled and gradual transition and greater welding surface area.

The tube member 514 can be formed from an inner polymer layer 509, an outer polymer layer 511, and a reinforcement member 513 disposed between the polymer layers. The inner polymer layer 509 can be composed of, or coated with, silicone, polytetrafluoroethylene (PTFE) or another lubricious material to provide a slippery surface for received interventional medical devices. The outer polymer 511 layer can include one or more soft, flexible materials, such as polyurethane, polyethylene or polyolefin of sequentially diminishing durometers along the tube member's 514 length, and it can be coated with a friction-reducing material (e.g., a hydrophilic or silicone coating) to facilitate insertion and trackability through vasculature and a guide catheter. Optionally, the outer polymer layer 511 can be loaded with one or more radiopaque elements for viewability under fluoroscopy. The reinforcing braid or coil 513 can be formed of stainless steel or a platinum alloy, for example, and can extend between the polymer layers along at least a portion of the tube member's 514 length. In an example, the reinforcing coil 513 is formed of 304 stainless steel having cross-sectional dimensions of 0.0015 in and 0.0080 in and is coupled with the distal end of the concave track's backbone support structure 503.

Figure 6:
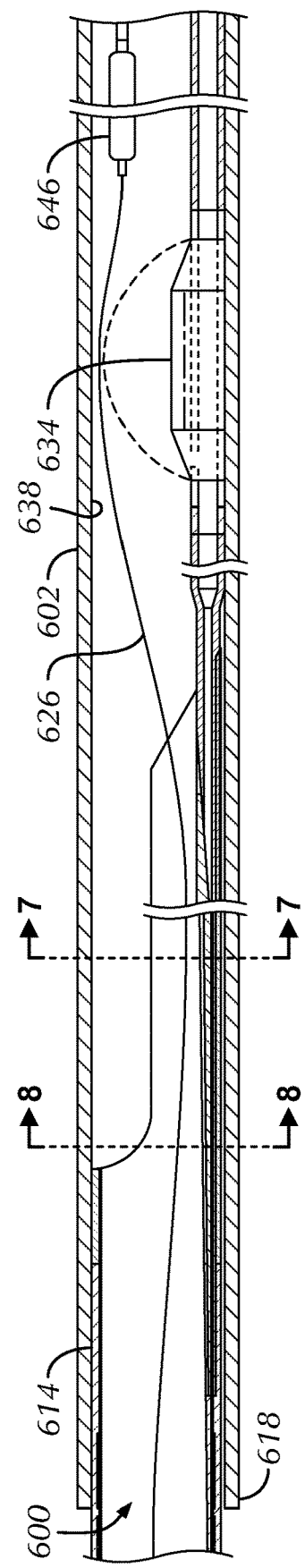
FIG. 6 illustrates a side cross-sectional view of a percutaneous device used in conjunction with a guide catheter, a guidewire and an OTW catheter, as constructed in accordance with at least one embodiment.

FIG. 6 illustrates a percutaneous device 600 disposed within a guide catheter 602 and used in conjunction with a guidewire 626 and an OTW dilatation balloon catheter 646. A tube member 614 of the percutaneous device 600 can be backloaded from its distal end onto a proximal end of the guidewire 626 and advanced through a hemostasis valve into the guide catheter 602. As shown, the tube member 614 of the percutaneous device 600 can be advanced beyond a distal end 618 of the guide catheter 602, such as about 10 cm or less beyond the distal end, under fluoroscopy. When so arranged, portions of the tube member 614 can engage an ostium and extend within a portion of a coronary artery to help maintain the position of the guide catheter 602 and improve access to the artery.

Once a fixation balloon 634 of the percutaneous device 600 is positioned within the guide catheter 602 as desired, it can be inflated (as shown in phantom) to restrict movement of the guidewire 626 (e.g., a rapid exchange length guidewire). The fixation balloon 634 can inflate to a diameter that fills the inner diameter of the guide catheter 602 (see FIGS. 7 and 8) and can engage the guidewire 626 against an inner surface 638 of the guide catheter 602, thereby inhibiting longitudinal movement of the guidewire 626 relative to the guide catheter 602 and an anatomic landmark (assuming the guide catheter 602 is stationary relative to the anatomic landmark). With the guidewire's 626 position locked by inflation of the fixation balloon 634, the proximal end of the guidewire 626 can be released by an operating physician and the OTW dilatation balloon catheter 646 can be backloaded over the guidewire 626 and advanced distally through the guide catheter 602.

Figure 7:
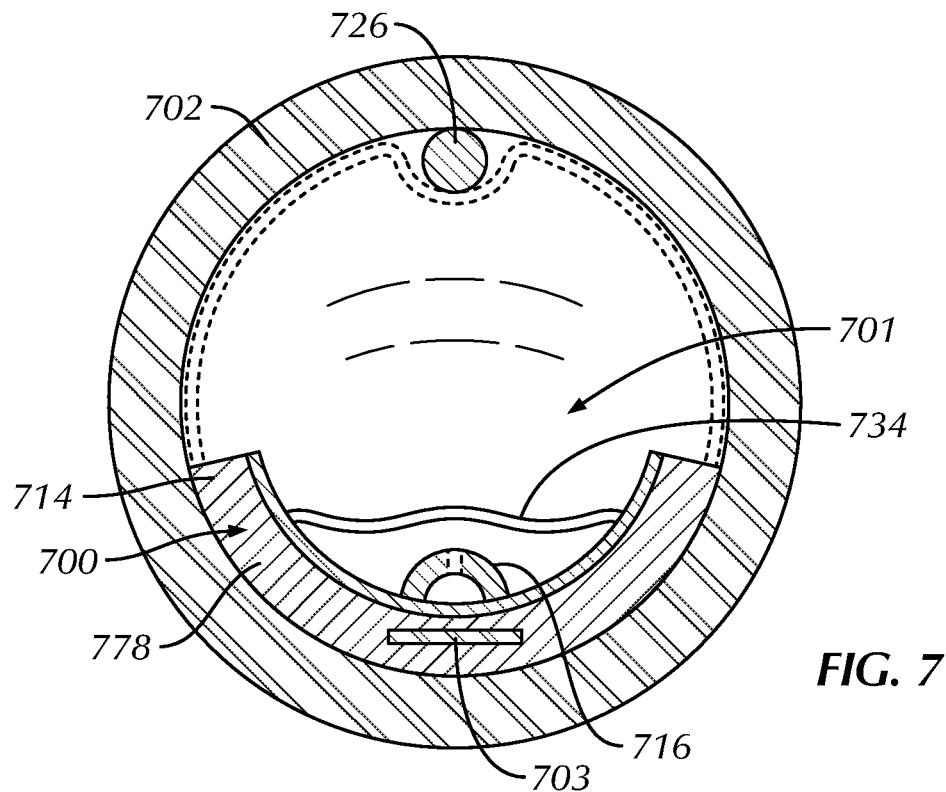
FIGS. 7-8 illustrate transverse cross-sectional views of a percutaneous device, a guide catheter and a guidewire, such as along lines 7-7 and 8-8, respectively, of FIG. 6.
Figure 8:
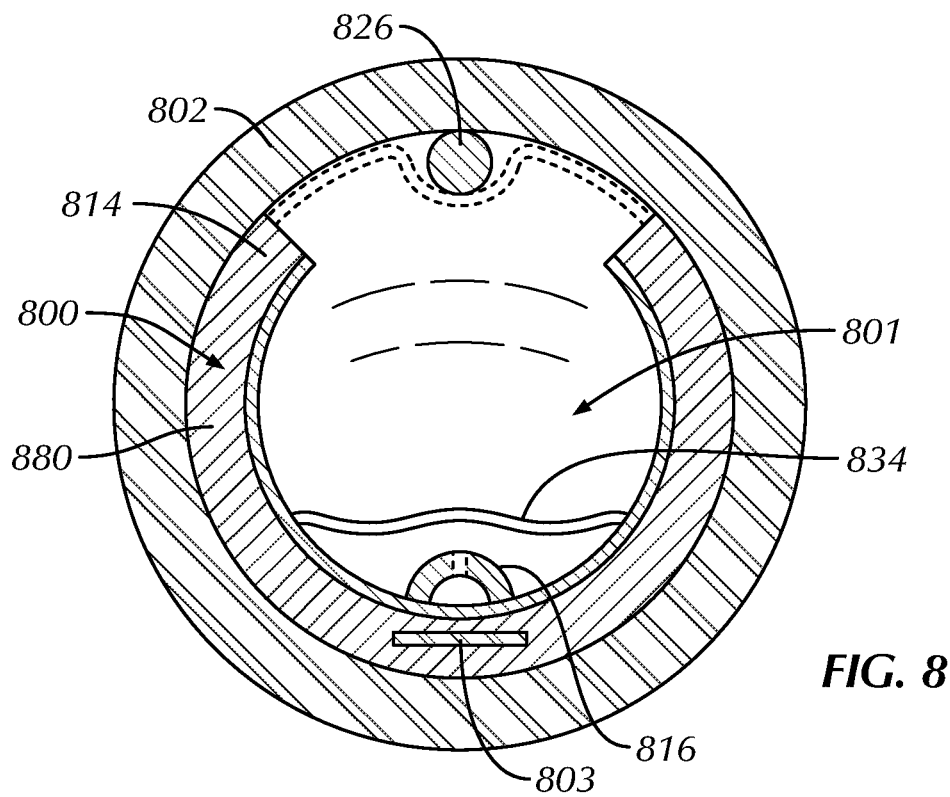

FIGS. 7 and 8 are transverse cross-sectional views of a percutaneous device 700, 800, a guide catheter 702, 802, and a guidewire 726, 826, such as along lines 7-7 and 8-8, respectively, of FIG. 6. It can be seen that the use of an eccentrically-positioned push member 716, 816 and backbone support structure 703, 803 to adjust a position of a tube member 714, 814 of the percutaneous device 700, 800 provides several advantages. The relatively small diameter of the push member 716, 816 creates low surface friction during its longitudinal movement within the guide catheter 702, 802. Low frictional force allows ease in extending and retrieving the tube member 714, 814. Also, the small cross-sectional size of the push member 716, 816 does not significantly interfere with the delivery of dilatation balloon catheters, stents and other interventional medical devices or fluids through the guide catheter 702, 802.

Delivery of dilatation balloon catheters, stents or other interventional medical devices through the guide catheter 702, 802 and into the tube member 714, 814 can be facilitated by a concave track 701, 801 defining a partially cylindrical opening and having a length of about 1 cm to 18 cm. The concave track 701, 801 can be positioned in the vicinity of a fixation balloon 734, 834 of the percutaneous device 700, 800 or can be positioned distal to the fixation balloon 734, 834. In an example, a first segment 778 of the concave track 701 can have an arcuate cross-sectional shape extending for a length of at least 0.5 cm and radially extending 25% to 40% of a cross-sectional circumference of the guide catheter 702 or tube member 714. A second segment 880 of the concave track 801 can have a hemicylindrical cross-sectional shape extending for a length of at least 0.5 cm and radially extending 40% to 70% of a cross-sectional circumference of the guide catheter 802 or tube member 814.

The push member 716, 816 and the fixation balloon 734, 834 can extend alongside the guidewire 726, 826 within the guide catheter 702, 802 and can remain there at all times during an interventional procedure. The fixation balloon 734, 834 can provide sufficient engagement to secure a position of the guidewire 726, 826 within the guide catheter 702, 802 when advancing or withdrawing a dilatation balloon catheter, for example, and can be deflated to allow for continued advancement of the dilatation balloon catheter relative to an anatomic landmark when a proximal end portion of the guidewire can be held by an operating physician.

Figure 9:
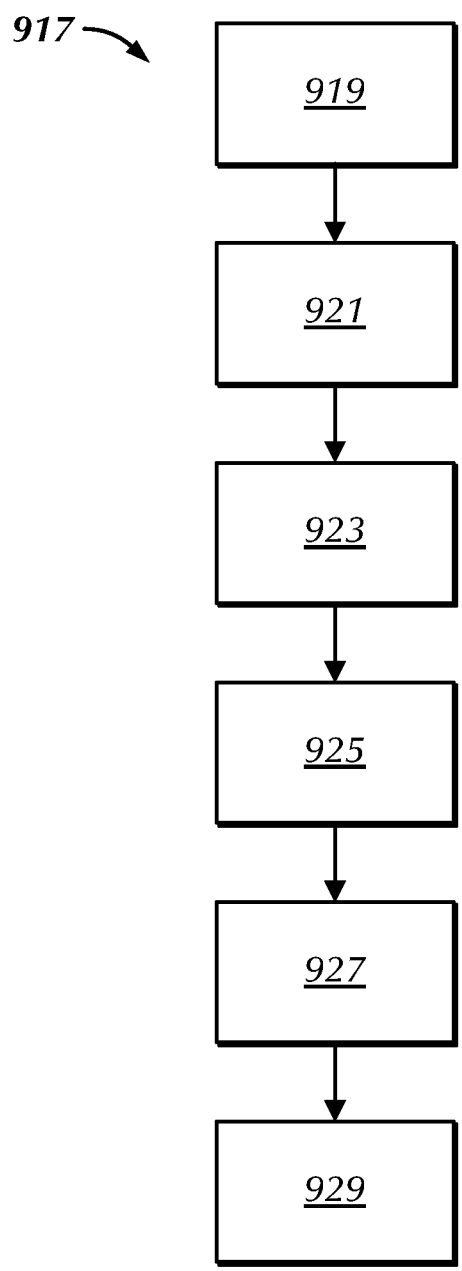
FIG. 9 illustrates a method of using a percutaneous device to exchange a first OTW catheter or other interventional medical device for a second OTW catheter or other interventional medical device using a guidewire as a rail, as constructed in accordance with at least one embodiment.

FIG. 9 illustrates an example method 917 of using a percutaneous device to exchange a first OTW catheter or other interventional medical device for a second OTW catheter or other interventional medical device using a guidewire as a rail.

The first OTW catheter can initially be removed from a patient. At 919, the first OTW catheter to be removed can be withdrawn over the guidewire and into a guide catheter until its distal end is positioned proximal of a fixation mechanism. This positioning can be confirmed using fluoroscopy and a radiopaque marker on or within the fixation mechanism. The fixation mechanism can then be increased in size (e.g., inflated) at 921 to engage the guidewire against an inner surface of the guide catheter, thereby preventing longitudinal movement of the guidewire during catheter removal. At 923, the first OTW catheter can be fully withdrawn and removed from the patient.

The second OTW catheter can then be inserted within the patient. At 925, the second OTW catheter can be loaded onto the locked guidewire and advanced distally toward the fixation mechanism until a proximal end of the guidewire becomes accessible outside of a proximal end of the second OTW catheter. At 927, a physician can grasp the proximal end of the guidewire and the fixation mechanism can be decreased in size (e.g., deflated). At 929, the second OTW catheter can be further directed into a desired target vessel or other hollow structure to provide a treatment.

Closing Notes:

It is often necessary in minimally invasive procedures to exchange one catheter or other interventional medical device for another while maintaining an indwelling position of a guidewire relative to a guide catheter or an anatomic landmark. Maintaining a position of the guide catheter relative to an ostium of a target vessel or other hollow structure in which the anatomic landmark is located can also be beneficial during the exchange. To maintain the position of the guidewire, guidewire lengths of about 270 cm or more and requiring two operators—a physician and his/her assistant—to handle were previously used, particularly when use of an OTW catheter was anticipated. One of the operators manipulated the long guidewire and held it in position while the other operator exchanged the catheters. The operators had to communicate with each other during the exchange, which led to increased procedure times, and the guidewire's tip had to be fluoroscopically monitored, which subjected the operators and patient to increased radiation exposure. In addition, the long length of the guidewire was awkward to handle and occasionally came in contact with an operating room floor or otherwise became contaminated requiring its disposal.

The present percutaneous devices and methods allow for the indwelling position of a guidewire to be maintained relative to a guide catheter, a tube member of the percutaneous device, or an anatomic landmark during a catheter exchange without the previously required task of holding the guidewire by hand from outside a patient's body. Since the guidewire no longer must be continually held from outside the body and is distally secured, the guidewire's length can be shorter and the dangerous, prolonged use of fluoroscopy is no longer necessary to continuously monitor guidewire position. A shorter guidewire allows a single operator to efficiently perform an OTW dilatation balloon catheter exchange. The devices and methods further allow for the position of the guide catheter to be maintained relative to an ostium of a target vessel or other hollow structure in which the anatomic landmark is located through the use of the tube member and its partial extension beyond a distal end of the guide catheter.

The above Detailed Description includes references to the accompanying drawings, which form a part of the Detailed Description. The Detailed Description should be read with reference to the drawings. The drawings show, by way of illustration, specific embodiments in which the present devices and methods can be practiced. These embodiments are also referred to herein as "examples."

The above Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a percutaneous device for use with a guide catheter and a guidewire can comprise an elongate tube member, a push member, and a fixation mechanism. The tube member can define a lumen sized to receive one or more interventional medical devices therethrough and can have an outer diameter smaller than a lumen of the guide catheter. The push member can be attached to the tube member for slidably positioning the tube member within or partially beyond the guide catheter. The fixation mechanism can be positioned on a portion of the push member and can be configured to engage the guidewire against the inner surface of the guide catheter or the tube member when moved or increased in size.

In Example 2, the percutaneous device of Example 1 can optionally be configured such that the tube member is more flexible than the push member.

In Example 3, the percutaneous device of any one of Examples 1 or 2 can optionally be configured such that the tube member includes a length of at least 6 cm.

In Example 4, the percutaneous device of any one or any combination of Examples 1-3 can optionally be configured such that a diameter of the lumen of the tube member is not more than one French size smaller than a diameter of the lumen of the guide catheter.

In Example 5, the percutaneous device of any one or any combination of Examples 1-4 can optionally be configured such that the tube member is movable between a first retracted position, in which the tube member is entirely positioned within the guide catheter, and a second extended position, in which a portion of the tube member extends beyond a distal end of the guide catheter.

In Example 6, the percutaneous device of any one or any combination of Examples 1-5 can optionally be configured such that the tube member includes an inner polymer layer, an outer polymer layer, and a reinforcement member disposed between the inner and outer polymer layers.

In Example 7, the percutaneous device of any one or any combination of Examples 1-6 can optionally be configured such that the push member is attached to a proximal end portion of the tube member.

In Example 8, the percutaneous device of any one or any combination of Examples 1-7 can optionally be configured such that the push member is eccentrically-positioned relative to a transverse cross-section of the tube member.

In Example 9, the percutaneous device of any one or any combination of Examples 1-8 can optionally be configured such that the fixation mechanism is a fixation balloon configured to engage the guidewire against the inner surface of the guide catheter or the tube member when inflated.

In Example 10, the percutaneous device of Example 9 can optionally be configured such that the push member includes a lumen in fluid communication with an interior of the fixation balloon for delivering inflation fluid to, or removing inflation fluid from, the fixation balloon.

In Example 11, the percutaneous device of Example 10 can optionally be configured such that the push member includes a hypotube.

In Example 12, the percutaneous device of any one of Examples 10 or 11 can optionally be configured such that a proximal end portion of the push member includes an inflation manifold couplable to a syringe or other inflation device.

In Example 13, the percutaneous device of any one or any combination of Examples 9-12 can optionally be configured such that the fixation balloon is positioned proximal to the tube member and is wrapped about the push member.

In Example 14, the percutaneous device of any one or any combination of Examples 9-13 can optionally be configured such that the fixation balloon includes an inner polymer layer and an outer polymer layer.

In Example 15, the percutaneous device of any one or any combination of Examples 9-14 can optionally further comprise an inflation indicator bulb positioned on a proximal end portion of the push member. The indicator bulb can be in fluid communication with the interior of the fixation balloon.

In Example 16, the percutaneous device of any one or any combination of Examples 1-15 can optionally be configured such that a center of the fixation mechanism is offset relative to an axial plane of the push member.

In Example 17, the percutaneous device of any one or any combination of Examples 1-16 can optionally further comprise a radiopaque marker positioned on or within the fixation mechanism.

In Example 18, the percutaneous device of any one or any combination of Examples 1-17 can optionally further comprise a concave track defining a partially cylindrical opening leading into a fully-round portion of the tube member.

In Example 19, the percutaneous device of Example 18 can optionally be configured such that a first segment of the concave track includes an arcuate cross-sectional shape.

In Example 20, the percutaneous device of Example 19 can optionally be configured such that the arcuate cross-sectional shape extends for a length of at least 0.5 cm.

In Example 21, the percutaneous device of any one of Examples 19 or 20 can optionally be configured such that the arcuate cross-sectional shape radially extends 25% to 40% of a cross-sectional circumference of the tube member.

In Example 22, the percutaneous device of any one or any combination of Examples 19-21 can optionally be configured such that a second segment of the concave track includes a hemicylindrical cross-sectional shape.

In Example 23, the percutaneous device of Example 22 can optionally be configured such that the hemicylindrical cross-sectional shape extends for a length of at least 0.5 cm.

In Example 24, the percutaneous device of any one of Examples 22 or 23 can optionally be configured such that the hemicylindrical cross-sectional shape radially extends 40% to 70% of a cross-sectional circumference of the tube member.

In Example 25, the percutaneous device of any one or any combination of Examples 18-24 can optionally be configured such that a support structure of the concave track transitions from the push member, in the form of a hypotube, to a lumen-less metallic structure.

In Example 26, the percutaneous device of Example 25 can optionally be configured such that a distal end of the hypotube and a proximal end of the lumen-less metallic structure include mating non-perpendicular cuts, which are welded together.

In Example 27, a method can comprise advancing a percutaneous device into a guide catheter and inhibiting longitudinal movement of a guidewire relative to the guide catheter or a tube member of the percutaneous device. The percutaneous device can include a push member, the tube member, and a fixation mechanism. Movement of the guidewire can be inhibited by increasing a size of the fixation mechanism, thereby engaging a portion of the guidewire against an inner surface of the guide catheter or the tube member.

In Example 28, prior to increasing the size of the fixation mechanism, the method of Example 27 can optionally further comprise withdrawing an interventional medical device over the guidewire until its distal end is positioned proximal of the fixation mechanism.

In Example 29, after increasing the size of the fixation mechanism, the method of any one or Examples 27 or 28 can optionally further comprise releasing contact with a proximal end portion of the guidewire.

In Example 30, after increasing the size of the fixation mechanism, the method of any one or any combination of Examples 27-29 can optionally further comprise advancing an interventional medical device over the guidewire to a location proximal of the fixation mechanism.

In Example 31, the method of Example 30 can optionally be configured such that advancing the interventional medical device over the guidewire to the location proximal of the fixation mechanism includes exposing a proximal end portion of the guidewire from a proximal end portion of the interventional medical device.

In Example 32, the method of Example 31 can optionally further comprise grasping the proximal end portion of the guidewire, decreasing the size of the fixation mechanism to disengage the guidewire from the inner surface of the guide catheter or the tube member, and advancing the interventional medical device over a distal end portion of the guidewire and through the tube member.

In Example 33, the method of Example 32 can optionally be configured such that decreasing the size of the fixation mechanism includes deflating a fixation balloon.

In Example 34, the method of any one or any combination of Examples 27-33 can optionally be configured such that advancing the percutaneous device into the guide catheter includes positioning the tube member in coaxial alignment with the guide catheter with its distal end portion extending beyond a distal end of the guide catheter.

In Example 35, the method of any one or any combination of Examples 27-34 can optionally be configured such that increasing the size of the fixation mechanism includes inflating a fixation balloon.

In Example 36, the percutaneous device or method of any one or any combination of Examples 1-35 can optionally be configured such that all components or options recited are available to use or select from.

Certain terms are used throughout this patent document to refer to particular features or components. As one skilled in the art will appreciate, different people may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" refers to a range of numbers that one of skill in the art considers equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to an operating physician. "Distal" and "distally" refer to a position that is distant from, or in a direction away from, the physician. "Proximal" and "proximally" refer to a position that is near, or in a direction toward, the physician.

The scope of the present devices and methods should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The claims of the present application are different and possibly broader than the claims pursued in the parent or related applications. To the extent any amendments or characterizations of the scope of any claim or referenced art during prosecution of the parent or related applications may be construed as a disclaimer of any subject matter supported by the present disclosure. Applicant hereby rescinds and retracts such disclaimer. Accordingly, the references construed in the parent or related applications may need to be revisited.

The Abstract is provided to allow the reader to quickly ascertain the nature of the technical disclosure. It is submitted with the understanding that it will not be used to interpret or limit the scope or meaning of the claims.

What is claimed is:

1. A method, comprising:
   advancing a guide extension catheter comprising a push member, an elongate tube member including a lumen having a diameter larger than a maximum outer dimension of the push member, and a fixation mechanism into a guide catheter; and
   inhibiting longitudinal movement of a guidewire relative to the guide catheter or the tube member, including increasing a size of the fixation mechanism to engage the guidewire against an inner surface of the guide catheter or against an inner surface of the tube member, wherein when the fixation mechanism is positioned proximal to the tube member, the guidewire is engaged against the inner surface of the guide catheter.

2. The method of claim 1, further comprising identifying a position of the fixation mechanism relative to the guide catheter or relative to patient anatomy using a radiopaque marker positioned proximate the fixation mechanism.

3. The method of claim 1, wherein inhibiting longitudinal movement of the guidewire relative to the guide catheter or relative to the tube member includes inhibiting longitudinal movement of a rapid exchange guidewire, having a length of 190 centimeters of less, relative to the guide catheter or relative to the tube member.

4. The method of claim 1, wherein increasing the size of the fixation mechanism includes delivering inflation fluid to the fixation mechanism by way of a lumen in the push member.

5. The method of claim 4, further comprising coupling an inflation device including the inflation fluid to an inflation manifold attached to a proximal end of the push member.

6. The method of claim 1, wherein engaging the guidewire against the inner surface of the guide catheter or against the inner surface of the tube member includes engaging the distal end portion of the guidewire against the inner surface of the guide catheter or of the tube member.

7. The method of claim 1, further comprising, prior to increasing the size of the fixation mechanism, withdrawing an interventional treatment device over the guidewire until its distal end is positioned proximal of the fixation mechanism.

8. The method of claim 1, further comprising, after increasing the size of the fixation mechanism, releasing user contact with a proximal end portion of the guidewire.

9. The method of claim 8, further comprising, after releasing user contact with the proximal end portion of the guidewire, withdrawing an interventional treatment device from the guide catheter.

10. The method of claim 1, further comprising, after increasing the size of the fixation mechanism, advancing an interventional treatment device over the guidewire to a location proximal of the fixation mechanism.

11. The method of claim 10, wherein advancing the interventional treatment device over the guidewire to the location proximal of the fixation mechanism includes advancing a balloon catheter or a stent catheter to the location proximal of the fixation mechanism.

12. The method of claim 10, wherein advancing the interventional treatment device over the guidewire to the location proximal of the fixation mechanism includes exposing a proximal end portion of the guidewire from a lumen of the interventional treatment device.

13. The method of claim 12, wherein exposing the proximal end portion of the guidewire from the lumen of the interventional treatment device includes exposing the proximal end portion of the guidewire from a full catheter length over-the-wire lumen of the interventional treatment device.

14. The method of claim 12, wherein exposing the proximal end portion of the guidewire from the lumen of the interventional treatment device includes exposing the proximal end portion of the guidewire from a rapid exchange lumen of the interventional treatment device.

15. The method of claim 12, further comprising grasping by the user of the exposed proximal end portion of the guidewire, decreasing the size of the fixation mechanism to disengage the guidewire from the inner surface of the guide catheter or of the tube member, and advancing one or both of the guidewire or the interventional treatment device through the tube member.

16. The method of claim 15, wherein decreasing the size of the fixation mechanism includes deflating a fixation balloon.

17. The method of claim 1, wherein advancing the guide extension catheter into the guide catheter includes positioning the tube member in coaxial alignment with the guide catheter with its distal end portion extending beyond a distal end of the guide catheter.

18. The method of claim 1, wherein tube member is one French size smaller than the guide catheter.

19. A method, comprising
advancing a guide extension catheter comprising a push member, an elongate tube member including a lumen having a diameter larger than a maximum outer dimension of the push member, and a fixation mechanism into a guide catheter; and
inhibiting longitudinal movement of a guidewire relative to the guide catheter or the tube member, including increasing a size of the fixation mechanism to engage the guidewire against an inner surface of the guide catheter or against an inner surface of the tube member, wherein when the fixation mechanism is positioned within the tube member, the guidewire is engaged against the inner surface of the tube member.

* * * * *